(12) United States Patent
Ward et al.

(10) Patent No.: US 10,198,825 B2
(45) Date of Patent: Feb. 5, 2019

(54) METHOD AND APPARATUS FOR ANALYZING THREE-DIMENSIONAL IMAGE DATA OF A TARGET REGION OF A SUBJECT

(71) Applicant: LONDON HEALTH SCIENCES CENTRE RESEARCH INC., London, Ontario (CA)

(72) Inventors: Aaron Ward, London (CA); David Palma, London (CA); Sarah Mattonen, London (CA); Suresh Senan, Amsterdam (NL)

(73) Assignees: LONDON HEALTH SCIENCES CENTRE RESEARCH INC., London, Ontario (CA); Suresh Senan, Amsterdam (NL)

(*) Notice: Subject to any disclaimer, the term of this patent is extended or adjusted under 35 U.S.C. 154(b) by 0 days.

(21) Appl. No.: 15/032,543

(22) PCT Filed: Oct. 28, 2014

(86) PCT No.: PCT/CA2014/000771
§ 371 (c)(1),
(2) Date: Apr. 27, 2016

(87) PCT Pub. No.: WO2015/061882
PCT Pub. Date: May 7, 2015

(65) Prior Publication Data
US 2016/0260224 A1    Sep. 8, 2016

Related U.S. Application Data

(60) Provisional application No. 61/896,349, filed on Oct. 28, 2013.

(51) Int. Cl.
*G06K 9/00* (2006.01)
*G06T 7/40* (2017.01)
(Continued)

(52) U.S. Cl.
CPC ............. *G06T 7/40* (2013.01); *A61B 6/032* (2013.01); *A61B 6/466* (2013.01); *A61B 6/5211* (2013.01);
(Continued)

(58) Field of Classification Search
CPC .. G06T 5/50; G06T 7/0081; G06T 7/11; G06T 7/187; G06T 7/0012; G06T 7/40;
(Continued)

(56) References Cited

U.S. PATENT DOCUMENTS

| 7,383,237 B2* | 6/2008 | Zhang | G06K 9/623 |
| | | | 706/20 |
| 8,045,770 B2* | 10/2011 | Reeves | G06T 7/0012 |
| | | | 382/128 |

(Continued)

FOREIGN PATENT DOCUMENTS

EP    2793164 A1 * 10/2014    ........... G06K 9/0014

OTHER PUBLICATIONS

Lambin et al., "Radiomics: Extracting more information from medical images using advanced feature analysis", European Journal of Cancer, (Mar. 2012), vol. 48, Issue 4, pp. 441-446.
(Continued)

*Primary Examiner* — Jose L Couso
(74) *Attorney, Agent, or Firm* — Ohlandt, Greeley, Ruggiero & Perle, LLP

(57) ABSTRACT

A method for analyzing three-dimensional image data of a target region of a subject, the method comprising identifying a region of interest within the target region containing imaging information predictive of a disease state of the target region, calculating at least two radiomic features associated with the region of interest, and classifying the region of interest based on the calculated radiomic features.

23 Claims, 9 Drawing Sheets

(51) Int. Cl.
  *G06T 7/00*  (2017.01)
  *A61B 6/03*  (2006.01)
  *A61B 6/00*  (2006.01)
  *G06K 9/62*  (2006.01)
  *G06T 7/11*  (2017.01)
  *G06F 19/00*  (2018.01)

(52) U.S. Cl.
  CPC ............ *A61B 6/5217* (2013.01); *G06F 19/00* (2013.01); *G06K 9/6269* (2013.01); *G06T 7/0012* (2013.01); *G06T 7/11* (2017.01); *G06T 2200/04* (2013.01); *G06T 2207/10081* (2013.01); *G06T 2207/20076* (2013.01); *G06T 2207/20104* (2013.01); *G06T 2207/30016* (2013.01); *G06T 2207/30056* (2013.01); *G06T 2207/30061* (2013.01); *G06T 2207/30081* (2013.01); *G06T 2207/30084* (2013.01); *G06T 2207/30096* (2013.01)

(58) Field of Classification Search
  CPC ....... G06T 2200/04; G06T 2207/10056; G06T 2207/10081; G06T 2207/10088; G06T 2207/20076; G06T 2207/20104; G06T 2207/30004; G06T 2207/30008; G06T 2207/30016; G06T 2207/30024; G06T 2207/30028; G06T 2207/30056; G06T 2207/30061; G06T 2207/30068; G06T 2207/30081; G06T 2207/30084; G06T 2207/30088; G06T 2207/30092; G06T 2207/30096; G06T 2210/41; A61B 5/055; A61B 5/0013; A61B 5/0022; A61B 5/0033; A61B 5/0082; A61B 5/4583; A61B 5/48; A61B 5/7275; A61B 5/7282; A61B 8/5223; A61B 6/032; A61B 6/466; A61B 6/5211; A61B 6/5217; A61B 10/02; A61B 2505/00; A61B 2576/00; A61N 5/1038; A61N 2005/1041; G06K 9/00127; G06K 9/00496; G06K 9/0014; G06K 9/00147; G06K 9/6267; G06K 9/6277; G06K 9/6269; G06K 9/469; G06K 9/6231; G06K 9/6296; G06K 2209/05–2209/055; G06K 2209/07; G01N 33/5076; G01N 33/483; G01N 33/4833; G01N 33/574; G01N 2033/57403; G01N 33/57407–33/57449; G01N 2033/57453–2033/57465; G01N 33/5026–33/5035; G01N 33/5047; G01N 33/5058; G01N 33/5067–33/5073; G01N 33/5091; G01N 2800/50; G01N 2800/52; G01N 2800/54; G01N 2800/60; G06F 3/048; G06F 19/30; G06F 19/321; G06F 19/322; G06F 19/342; G06F 19/3431; G06F 19/3418; G06F 19/3437; G06F 19/3443; G06F 19/3456; G06F 19/325; G06F 19/3468; G06F 19/3481; G06F 19/3487; G06F 19/345; G06N 5/04; G06N 7/005; A61K 49/0004

See application file for complete search history.

(56) References Cited

U.S. PATENT DOCUMENTS

| | | | | |
|---|---|---|---|---|
| 8,488,863 | B2* | 7/2013 | Boucheron | G06K 9/0014 |
| | | | | 382/131 |
| 8,737,715 | B2* | 5/2014 | Zhukov | G01N 33/5076 |
| | | | | 382/133 |
| 9,275,451 | B2* | 3/2016 | Ben-Haim | G06F 19/321 |
| 9,536,305 | B2* | 1/2017 | Giger | G06K 9/6253 |
| 2010/0111396 | A1 | 5/2010 | Boucheron | |
| 2012/0177280 | A1 | 7/2012 | Zhukov et al. | |
| 2014/0184608 | A1* | 7/2014 | Robb | A61B 5/055 |
| | | | | 345/440 |
| 2016/0078613 | A1* | 3/2016 | Lambin | G06K 9/0014 |
| | | | | 382/131 |
| 2016/0140300 | A1* | 5/2016 | Purdie | G06F 19/327 |
| | | | | 705/2 |
| 2016/0203597 | A1* | 7/2016 | Chang | F23Q 3/004 |
| | | | | 382/128 |
| 2016/0203599 | A1* | 7/2016 | Gillies | A61B 6/463 |
| | | | | 382/132 |
| 2016/0260211 | A1* | 9/2016 | Gillies | G06T 7/41 |

OTHER PUBLICATIONS

Hunter, Luke, "Radiomics of NSCLC: Quantitative CT Image Feature Characterization and Tumor Shrinkage Prediction", May 2013 (May 2013). UT GSBS Dissertations and Theses (Open Access). Paper 330. Texas Medical Centre Library.

International Search Report dated Mar. 3, 2015 corresponding to International Patent Application No. PCT/CA2014/000771; 2 pages.

* cited by examiner

Neighbor Voxel Value (i)

|   | 1 | 2 | 3 | 4 | 5 | 6 | 7 | 8 | 9 | 10 |
|---|---|---|---|---|---|---|---|---|---|---|
| 1 | 0 | 1 | 0 | 0 | 0 | 0 | 0 | 0 | 0 | 0 |
| 2 | 1 | 0 | 1 | 0 | 0 | 0 | 0 | 0 | 0 | 0 |
| 3 | 0 | 1 | 0 | 1 | 0 | 0 | 0 | 0 | 0 | 0 |
| 4 | 0 | 0 | 1 | 9 | 1 | 0 | 0 | 0 | 0 | 0 |
| 5 | 0 | 0 | 0 | 1 | 0 | 1 | 0 | 0 | 0 | 0 |
| 6 | 0 | 0 | 0 | 0 | 1 | 0 | 1 | 0 | 0 | 0 |
| 7 | 0 | 0 | 0 | 0 | 0 | 1 | 0 | 1 | 0 | 0 |
| 8 | 0 | 0 | 0 | 0 | 0 | 0 | 1 | 9 | 1 | 0 |
| 9 | 0 | 0 | 0 | 0 | 0 | 0 | 0 | 1 | 0 | 1 |
| 10 | 0 | 0 | 0 | 0 | 0 | 0 | 0 | 0 | 1 | 0 |

Reference Voxel Value (j)

$g(i,j) = g(7,8) = 1$

METHOD AND APPARATUS FOR ANALYZING THREE-DIMENSIONAL IMAGE DATA OF A TARGET REGION OF A SUBJECT

FIELD

The subject disclosure relates generally to image processing and in particular, to a method and apparatus for analyzing three-dimensional image data of a target region of a subject.

BACKGROUND

Stereotactic ablative radiotherapy (SABR) is used to treat subjects with early stage non-small cell lung cancer (NSCLC) who are medically inoperable or refuse surgery[1]. SABR uses advanced treatment planning and delivery to treat tumors at a high dose, while sparing surrounding normal tissue. Multiple collimated radiation beams are used to achieve a dose distribution highly conformal to the shape of the tumor with steep dose gradients.

The imaging modality generally used for post-SABR follow up is computed tomography (CT). During follow-up assessment, a key clinical decision is whether to provide further, possibly more invasive intervention, such as for example surgery or chemotherapy, to treat or remove recurrent/residual disease. This clinical decision relies on the ability to assess the success of the SABR treatment, that is, to determine whether the subject's cancer will recur. Since recurrent lung cancer typically progresses quickly, a decision to proceed with further intervention is valuable if made early. Delayed detection of recurrence may reduce the options for salvage therapies. This clinical decision is complicated by the fact that following radiotherapy to the lung, radiation induced lung injury (RILI) may occur as radiation pneumonitis and radiation fibrosis which appear as an increase in lung density on CT[2,3]. Following treatment with SABR, RILI can have a similar size and morphology as a recurrent tumor[4,5] thereby making it difficult to differentiate between the two. Several studies have looked at the radiologic appearance of recurrence on follow-up CT post-SABR, and suggest that an enlarging opacity twelve (12) months after treatment is most suggestive of recurrence[6,7]. These studies also suggest that other imaging features, such as a bulging margin and disappearance of air bronchograms, are also suggestive of recurrence[8,9].

A means for predicting recurrence within six (6) months of treatment based on CT imaging would permit timely intervention for recurrence, which typically manifests after twelve (12) months. Radiomics, the extraction of a large number of quantitative image features such as size, shape and appearance, has been shown to have prognostic power in lung cancer[18]. Image texture analysis has been used for computer-aided diagnosis on lung CT, and second-order texture statistics based on grey-level co-occurrence matrices (GLCMs) have been shown to quantify lung abnormalities[10,11].

It is therefore an object to provide a novel method and apparatus for analyzing three-dimensional image data of a target region of a subject.

SUMMARY

Accordingly, in one aspect there is provided a method for analyzing three-dimensional image data of a target region of a subject, the method comprising identifying a region of interest within the target region containing imaging information predictive of a disease state of the target region, calculating at least two radiomic features associated with the region of interest, and classifying the region of interest based on the calculated radiomic features.

In an embodiment, the at least two radiomic features are calculated from gray-level co-occurrence matrices associated with the region of interest. The region of interest may be classified using a classifier such as a linear Bayes normal classifier, a quadratic Bayes normal classifier, or a support vector classifier. The step of identifying the region of interest may comprise detecting a region having ground glass opacity. The target region may be a subject's lung, liver, brain, prostate, kidney, head or neck. Each radiomic feature may be one of a first-order texture feature and a second-order texture feature.

In an embodiment, the first-order texture feature is one of mean absolute deviation and standard deviation.

In an embodiment, the second-order texture feature is one of energy, entropy, correlation, inverse difference moment, inertia, cluster shade, and cluster prominence.

In an embodiment, the step of classifying may comprise comparing the at least two radiomic features to a decision line. The region of interest may be classified as one of recurrent cancer and radiation induced lung injury.

In an embodiment, image data representing at least the region of interest may be presented on a display unit.

According to another aspect there is provided an apparatus for analyzing three-dimensional image data of a target region of a subject, the apparatus comprising memory storing three-dimensional image data of a target region of a subject, and at least one processor communicating with the memory and analyzing the three-dimensional image data, the processor configured to identify a region of interest within the target region containing imaging information predictive of a disease state associated with the target region, calculate at least two radiomic features associated with the target region, and classify the region of interest based on the calculated radiomic features.

According to another aspect there is provided a non-transitory computer-readable medium having stored thereon a computer program for execution by a computer to perform a method for analyzing three-dimensional image data of a target region of a subject comprising identifying a region of interest within the target region containing imaging information predictive of a disease state of the target region, calculating at least two radiomic features associated with the region of interest, and classifying the region of interest based on the calculated radiomic features.

BRIEF DESCRIPTION OF THE DRAWINGS

Embodiments will now be described by way of example only with reference to the accompanying drawings in which.

DETAILED DESCRIPTION OF EMBODIMENTS

Figure 1:
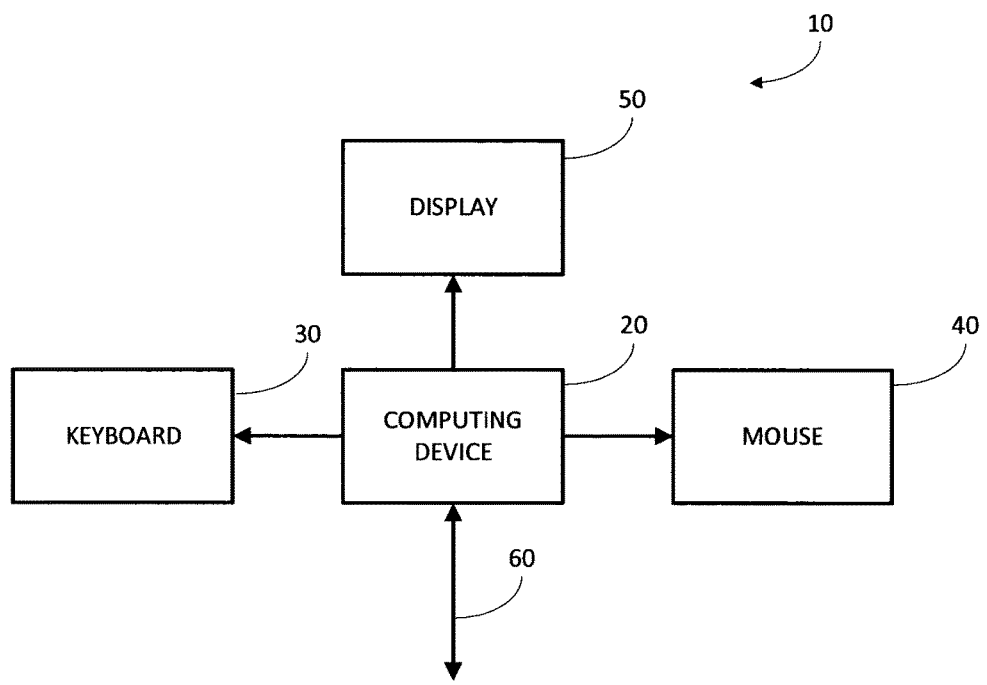
FIG. 1 is a block diagram of an apparatus for analyzing three-dimensional image data of a target region of a subject.

Turning now to FIG. 1, an apparatus for analyzing three-dimensional image data of a target region of a subject is shown and is generally identified by reference numeral 10. As can be seen, the apparatus comprises a general purpose computing device 20 that is coupled to a keyboard 30, a mouse 40 and a display unit 50. The general purpose computing device 20 is also coupled to an imaging device (not shown) such as for example a computed tomography (CT) imaging system via a bus system 60.

The general purpose computing device 20 in this embodiment is a personal computer or other suitable processing device comprising, for example, a processing unit comprising one or more processors, non-transitory system memory (volatile and/or non-volatile memory), other non-transitory non-removable or removable memory (e.g. a hard disk drive, RAM, ROM, EEPROM, CD-ROM, DVD, flash memory, optical data storage, etc.) and a system bus coupling the various computing device components to the processing unit. The general purpose computing device 20 may also comprise networking capabilities using Ethernet, WiFi, and/or other network formats, to enable access to shared or remote drives, one or more networked computers, or other networked devices.

Figure 2:
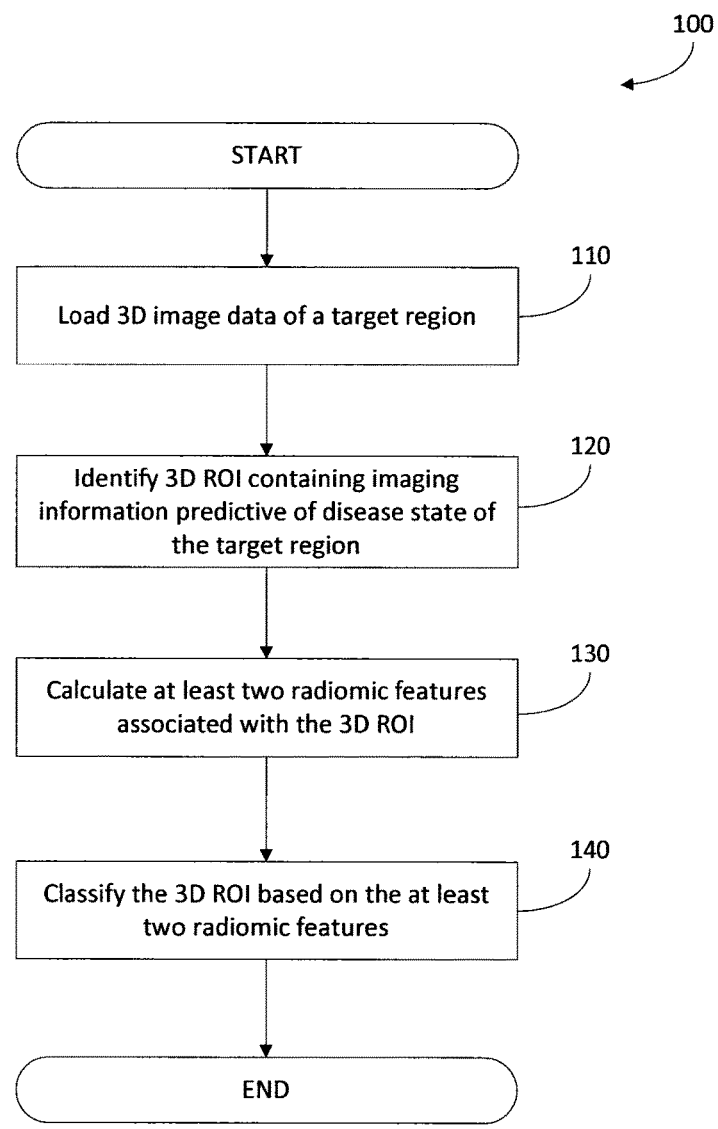
FIG. 2 is a flowchart showing a method for analyzing three-dimensional image data of a target region of a subject executed by the apparatus of FIG. 1.
Figure 3A:
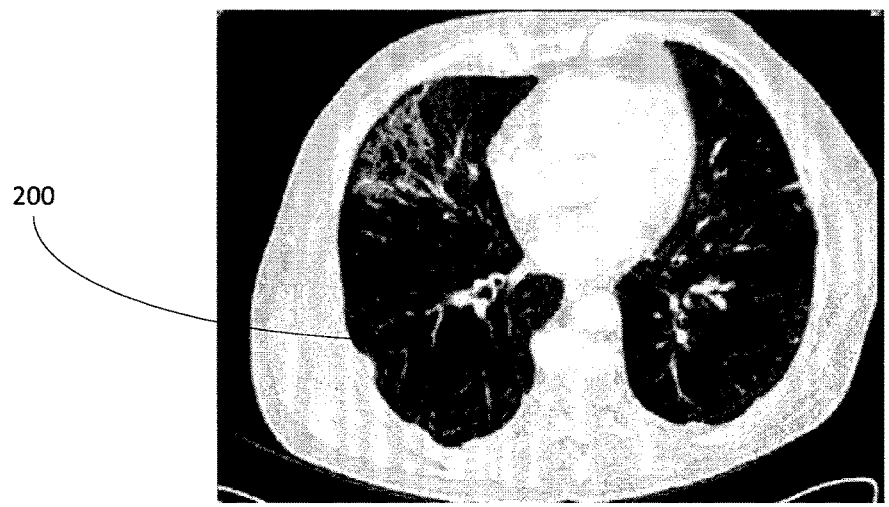
FIGS. 3A to 3D show various views of three-dimensional (3D) image data of a subject's lungs.
Figure 3B:
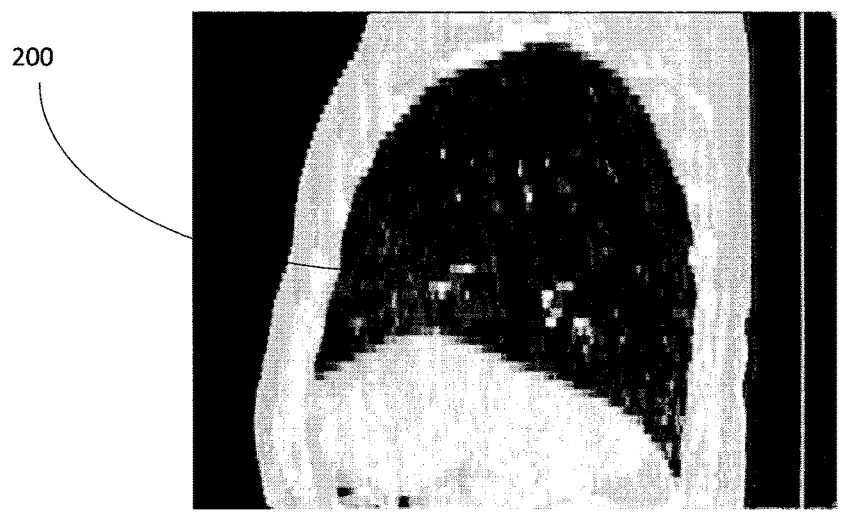
Figure 3C:
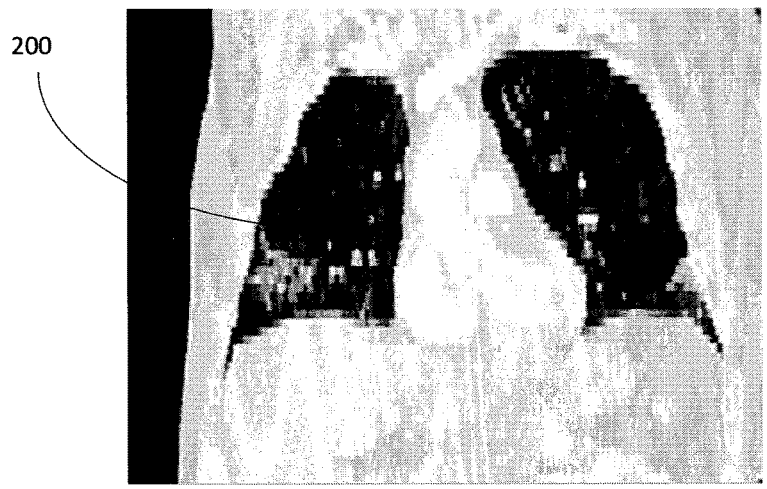
Figure 3D:
Figure 4A:
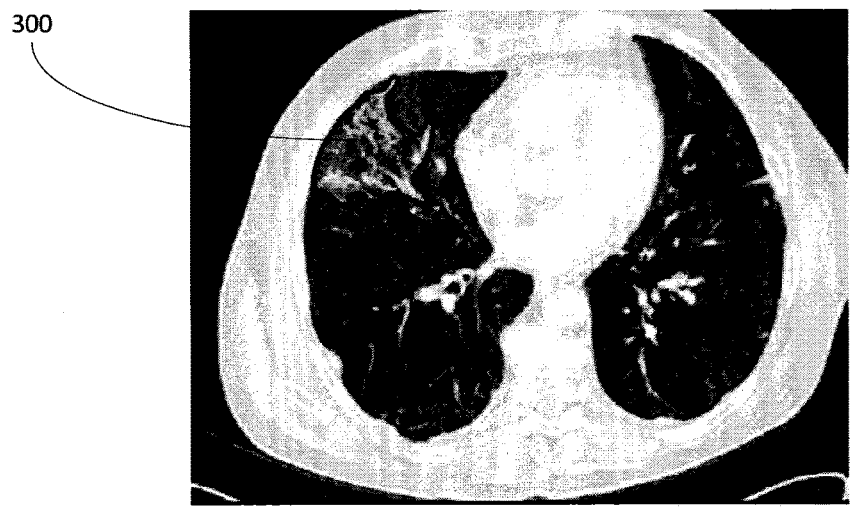
FIGS. 4A to 4C show various views of three-dimensional (3D) image data of a subject's lungs, identifying a three-dimensional (3D) region of interest therein.
Figure 4B:
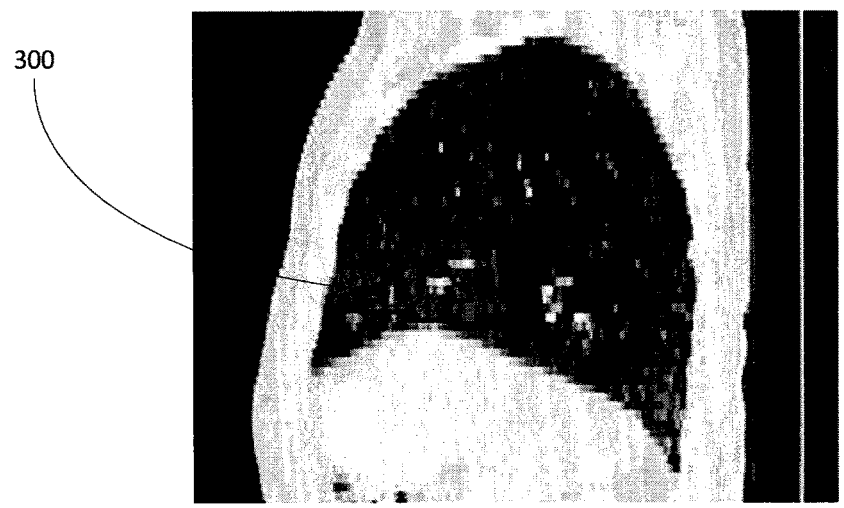
Figure 4C:
Figure 4D:
FIG. 4D shows the three-dimensional (3D) region of interest identified in FIGS. 4A to 4C.

In this embodiment, the general purpose computing device 20 receives three-dimensional (3D) image data of a target region of a subject obtained by the CT imaging system via the bus system 60. The 3D image data is stored in memory of the general purpose computing device 20 and comprises a series of two-dimensional (2D) image slices. Each 2D image slice comprises image elements such as for example pixels or voxels. The general purpose computing device 20 executes program code causing the general purpose computing device to analyze the 3D image data according to method 100 shown in FIG. 2.

Initially, during the 3D image data analyzing, the 3D image data of the target region is loaded for processing (step 110). As will be appreciated, portions of the 3D image data may contain imaging information that is useful for predicting a disease state associated with the target region, whereas other portions of the 3D image data may not. The loaded 3D image data is then analyzed to determine if a 3D region of interest (ROI) containing imaging information predictive of a disease state of the target region is identified (step 120). If so, the image data within the 3D ROI is analyzed. Portions of the 3D image data that do not contain imaging information that is useful for predicting a disease state associated with the target region (i.e. image data outside of the 3D ROI) are not analyzed. At least two radiomic features associated with the identified 3D ROI are then calculated (step 130) and the 3D ROI is classified based on the calculated radiomic features to predict a disease state of the target region (step 140). During execution of method 100, the general purpose computing device 20 may present 3D image data representing the target region (including the 3D ROI) on the display unit 50. The general purpose computing device 20 may also present 3D image data representing only the 3D ROI on the display unit 50.

Method 100 will again be described assuming that the target region is a subject's lungs. In this example, at step 110, 3D image data of the subject's lungs captured by the CT imaging system is loaded for processing. Exemplary 3D image data of the subject's lungs 200 is shown in FIGS. 3A to 3D. In this example, the 3D image data of the subject's lungs 200 comprises a plurality of image slices having a thickness of about 5 mm.

A 3D ROI is identified by determining one or more regions within the 3D image data that contain ground-glass opacity (GGO) (step 120). To identify the one or more regions that contain GGO, the 3D image data is segmented. The normal lung parenchyma density of each segmented region is compared to its surrounding regions. In the event that there is an increase in normal lung parenchyma density between the segmented region and its surrounding regions, the segmented region is identified as a GGO region.

In this example, the GGO regions are identified using the round brush tool in ITK-SNAP version 2.2.0 (www.itksnap.org) created by P. A. Yushkevich, J. Piven, H. C. Hazlett, R. G. Smith, S. Ho, J. C. Gee and G. Gerig and based on the publication entitled "User-guided 3D active contour segmentation of anatomical structures: significantly improved efficiency and reliability", NeuroImage 31, 1116-1128 (2006). Specifically, the regions are segmented using a lung window setting having a window width of 1500 Hounsfield units (HU) and a window level of −600 HU. A mediastinal window having a window width of 350 HU and window level of 40 HU is also used for delineation of any structures abutting the mediastinum. An exemplary 3D ROI 300 associated with the subject's lung 200 is shown in FIGS. 4A to 4D.

At least two radiomic features associated with the 3D ROI 300 are then calculated (step 130). In this example, two (2) first-order texture features and seven (7) second-order texture features are calculated based on Conners, Trivedi and Harlow feature sets[12,13]. The two (2) first-order texture features are the standard deviation SD and the mean absolute deviation MAD of intensities. The seven (7) second-order texture features are energy E, entropy S, correlation ρ, inverse difference moment IDM, inertia I, cluster shade SHADE, and cluster prominence PROM.

To calculate the first-order texture features, a vector v containing N intensity values within the 3D ROI 300 is formed by concatenating voxel intensities. The standard deviation SD is calculated according to Equation 1:

$$SD = \sqrt{\frac{1}{N-1} \sum_{i=1}^{N} (v_i - \bar{v})^2} \qquad (1)$$

The mean absolute deviation MAD is calculated according to Equation 2:

$$MAD = \sqrt{\frac{1}{N} \sum_{i=1}^{N} |v - \bar{v}|} \qquad (2)$$

Figures 5, 6:
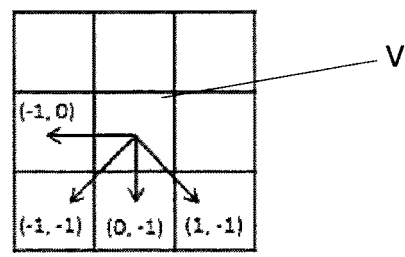
FIG. 5 shows an exemplary grey-level co-occurrence matrix (GLCM)
FIG. 6 shows four (4) exemplary spatial directions used to calculate four (4) GLCMs.

To calculate the second-order texture features, at least one gray-level co-occurrence matrix (GLCM) is calculated for the 3D ROI 300. An exemplary GLCM in the form of a 10×10 matrix is shown in FIG. 5. The size of each GLCM is dependent on the density of the GGO region(s), as will be described below. The GLCM is a two-dimensional square matrix g where the rows i and columns j correspond to observable gray levels within the 3D ROI 300. Specifically, each matrix element g(i,j) contains a non-negative integer indicating the number of neighboring voxel pairs whose elements have gray levels i and j. As shown, matrix element g(7, 8) contains an integer value of one (1), meaning that one (1) pair of neighboring voxel pairs within the 3D ROI contains gray levels of 7 (for the reference voxel) and 8 (for the neighbor voxel).

In this example, four (4) spatial directions are used for pairing neighboring voxels and as a result, four (4) GLCMs are calculated. The second-order texture features are calculated for each GLCM and are averaged over all four (4) spatial directions. As shown in FIG. 6, the four spatial directions are within the 2D axial image plane. Through-plane directions are not required due to anisotropy of the voxels (5 mm slice thickness). The four spatial directions for a particular voxel V are (−1, 0), (−1, −1), (0, −1) and (1, −1). As will be appreciated, in the event a voxel does not have a neighbor in a particular spatial direction, then that particular spatial direction is ignored.

Calculating the GLCM for each spatial direction requires the configuration of GLCM histogram bins. Histogram distributions of CT densities within the GGO region are analyzed to determine the appropriate number and density ranges of the bins for each GLCM. Within the GGO, the densities range from −1000 HU to 200 HU. The number of density bins in the GGO analysis is 60 bins, yielding 20 HU bin widths. As a result, each GLCM is a 60×60 matrix.

As shown below, the weighted voxel average µ and the weighted voxel variance σ are required for the calculation of the correlation ρ, the cluster shade SHADE and the cluster prominence PROM. The weighted voxel average µ is calculated according to Equation 3:

$$\mu = \Sigma_{i,j} i \cdot g(i,j) = \Sigma_{i,j} j \cdot g(i,j) \qquad (3)$$

The weighted voxel variance σ is calculated according to Equation 4:

$$\sigma = \Sigma_{i,j} (i-\mu)^2 \cdot g(i,j) = \Sigma_{i,j} (j-\mu)^2 \cdot g(i,j) \qquad (4)$$

As mentioned previously, seven second-order texture features are calculated. In this example, the second-order texture features are computed for all four (4) GLCM's and are averaged over all spatial directions. The equations used for each second-order texture feature will now be described.

Energy E represents the uniformity of the 3D ROI and is calculated according to Equation 5:

$$E = \Sigma_{i,j} g(i,j)^2 \qquad (5)$$

Entropy S represents the randomness of the GLCM and is calculated according to Equation 6:

$$S = -\Sigma_{i,j} g(i,j) \log_2 g(i,j) \qquad (6)$$

As will be appreciated, entropy S=0 if g(i,j)=0.

Correlation ρ represents how correlated each voxel in the 3D ROI is to its neighbor and is calculated according to Equation 7:

$$\rho = \Sigma_{i,j} \frac{(i-\mu)(j-\mu)g(i,j)}{\sigma^2} \qquad (7)$$

Inverse difference moment IDM represents the contrast in the 3D ROI and is calculated according to Equation 8:

$$IDM = \Sigma_{i,j} \frac{1}{1+(i-j)^2} g(i,j) \qquad (8)$$

Inertia I represents the contrast in the 3D ROI and is calculated according to Equation 9:

$$I = \Sigma_{i,j} (i-j)^2 g(i,j) \qquad (9)$$

Cluster shade SHADE represents the skewness of the GLCM and is calculated according to Equation 10:

$$SHADE = \Sigma_{i,j} ((i-\mu)+(j-\mu))^3 g(i,j) \qquad (10)$$

Cluster prominence PROM represents the skewness of the GLCM and is calculated according to Equation 11:

$$PROM = \Sigma_{i,j} ((i-\mu)+(j-\mu))^4 g(i,j) \qquad (11)$$

Figure 7:
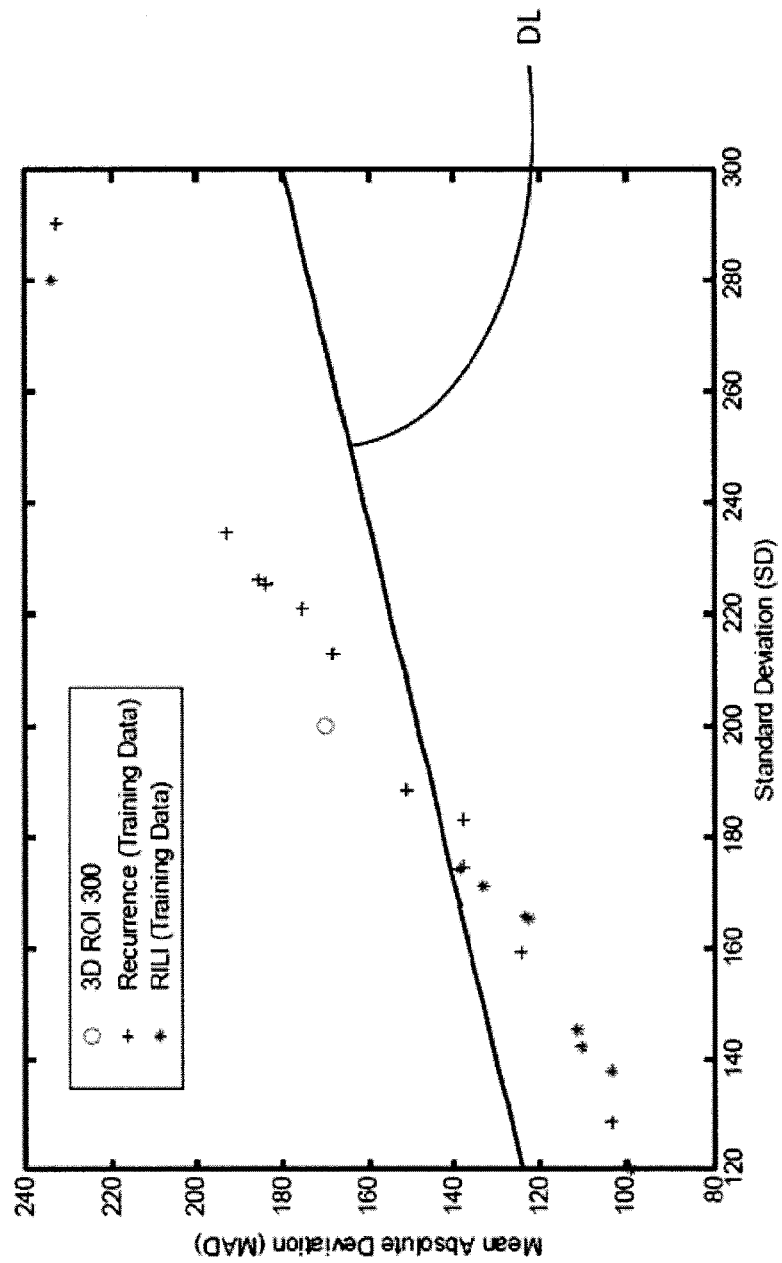
FIG. 7 shows a graph of Standard Deviation vs. Mean Absolute Deviation used to classify the three-dimensional (3D) region of interest of FIG. 4D according to a linear Bayes normal classifier.
Figure 8:
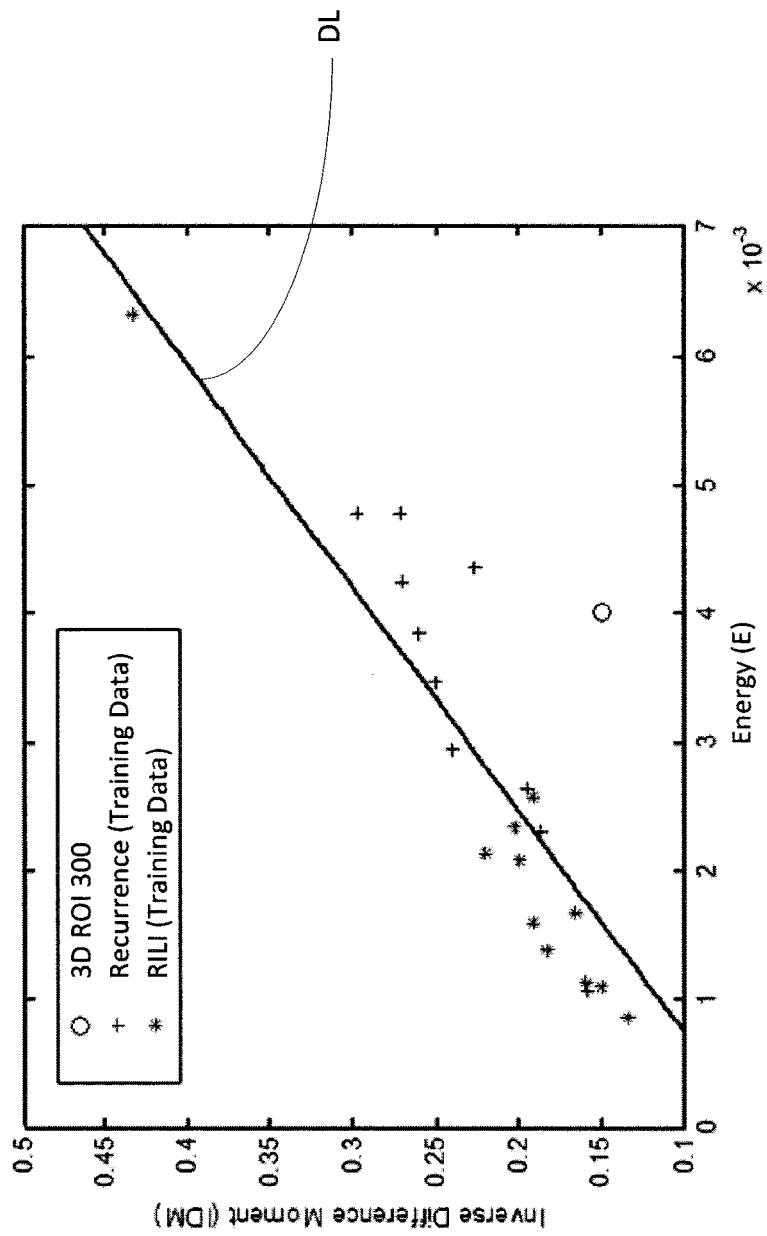
FIG. 8 shows a graph of Energy vs. Inverse Different Moment used to classify the three-dimensional (3D) region of interest of FIG. 4D according to a linear Bayes normal classifier.

A linear classifier is used to classify the 3D ROI based on a linear combination of two radiomic features (step 140). In this example, the linear classifier is a linear Bayes normal classifier[14–16]. The two radiomic features may be first-order texture features, second-order texture features, or a combination thereof. FIG. 7 shows a linear combination of first-order texture features, in particular standard deviation SD and mean absolute deviation MAD. FIG. 8 shows a linear combination of second-order texture features, in particular Energy E and inverse difference moment IDM. In both FIGS. 7 and 8, a decision line DL is used. The decision line DL is generated based on a training data set. The training data set is a data set comprising a number of 3D image data sets having 3D ROI's classified as "recurrent cancer" or "radiation induced lung injury" based on decisions made by medical experts. As such, the linear Bayes normal classifier is trained to classify a 3D ROI as "recurrent cancer" or "radiation induced lung injury" based on its position relative to the decision line DL. As shown in FIGS. 7 and 8, the 3D ROI 300 is classified as "recurrent cancer".

As mentioned previously, the general purpose computer device 20 may present 3D image data representing the subject's lungs (including the 3D ROI 300) on the display unit 50. The general purpose computing device 20 may also present 3D image data representing only the 3D ROI 300 on the display unit 50.

Although in embodiments described above the apparatus 10 is described as processing 3D images received from a CT imaging device, those skilled in the art will appreciate that 3D images received from other imaging devices such as for example magnetic resonance (MR) imaging devices, ultrasound imaging devices, positron emitting tomography (PET) imaging devices, light and fluorescence microscopy imaging devices, x-ray imaging devices, etc. may be processed.

Although in embodiments described above the classification is performed using the linear Bayes normal classifier, those skilled in the art will appreciate that other classifiers may be used such as for example the quadratic Bayes normal classifier[14,15] or the support vector classifier[17].

Although in embodiments described above the 3D ROI is identified by using ground-glass opacity, those skilled in the art will appreciate that alternatives are available. For example, in another embodiment, consolidation may be used. In this example, the 3D ROI is identified by determining one or more regions within the 3D image data that contain consolidation. The consolidation regions may be identified by segmenting regions of the 3D image data having an increase in tissue density with respect to their surrounding region, with no blood vessels being visible therewithin.

Although in embodiments described above the target region is the subject's lungs, those skilled in the art will appreciate that other target regions may be classified such as for example the subject's liver, brain, prostate, kidney, head or neck.

Although in embodiments above the method and apparatus for analyzing three-dimensional image data of a target region of a subject is described as being executed by a general purpose computing device, those skilled in the art will appreciate that the method and apparatus may be part of an imaging system such as for example a computed tomography (CT) imaging system.

Although embodiments have been described above with reference to the accompanying drawings, those of skill in the art will appreciate that other variations and modifications may be made without departing from the scope thereof as defined by the appended claims.

REFERENCES

1. D. J. Hoopes, M. Tann, J. W. Fletcher, J. A. Forquer, P. F. Lin, S. S. Lo, R. D. Timmerman and R. C. McGarry, "FDG-PET and stereotactic body radiotherapy (SBRT) for stage I non-small-cell lung cancer," Lung cancer (Amsterdam, Netherlands) 56, 229-234 (2007).
2. J. Van Dyk and R. P. Hill, "Post-irradiation lung density changes measured by computerized tomography," International journal of radiation oncology, biology, physics 9, 847-852 (1983).
3. K. Mah, P. Y. Poon, J. Van Dyk, T. Keane, I. F. Majesky and D. F. Rideout, "Assessment of acute radiation-induced pulmonary changes using computed tomography," Journal of computer assisted tomography 10, 736-743 (1986).
4. A. Takeda, E. Kunieda, T. Takeda, M. Tanaka, N. Sanuki, H. Fujii, N. Shigematsu and A. Kubo, "Possible misinterpretation of demarcated solid patterns of radiation fibrosis on CT scans as tumor recurrence in patients receiving hypofractionated stereotactic radiotherapy for lung cancer," International journal of radiation oncology, biology, physics 70, 1057-1065 (2008).
5. A. Linda, M. Trovo and J. D. Bradley, "Radiation injury of the lung after stereotactic body radiation therapy (SBRT) for lung cancer: a timeline and pattern of CT changes," European journal of radiology 79, 147-154 (2011).
6. Y. Matsuo, Y. Nagata, T. Mizowaki, K. Takayama, T. Sakamoto, M. Sakamoto, Y. Norihisa and M. Hiraoka, "Evaluation of mass-like consolidation after stereotactic body radiation therapy for lung tumors," International journal of clinical oncology/Japan Society of Clinical Oncology 12, 356-362 (2007).
7. S. Kato, A. Nambu, H. Onishi, A. Saito, K. Kuriyama, T. Komiyama, K. Marino and T. Araki, "Computed tomography appearances of local recurrence after stereotactic body radiation therapy for stage I non-small-cell lung carcinoma," Japanese journal of radiology 28, 259-265 (2010).
8. T. Ishimori, T. Saga, Y. Nagata, Y. Nakamoto, T. Higashi, M. Mamede, T. Mukai, Y. Negoro, T. Aoki, M. Hiraoka and J. Konishi, "18F-FDG and 11C-methionine PET for evaluation of treatment response of lung cancer after stereotactic radiotherapy," Annals of nuclear medicine 18, 669-674 (2004).
9. K. Huang, M. Dahele, S. Senan, M. Guckenberger, G. B. Rodrigues, A. Ward, R. G. Boldt and D. A. Palma, "Radiographic changes after lung stereotactic ablative radiotherapy (SABR)—Can we distinguish recurrence from fibrosis? A systematic review of the literature," Radiotherapy and oncology: journal of the European Society for Therapeutic Radiology and Oncology 102, 335-342 (2012).
10. P. D. Korfiatis, A. N. Karahaliou, A. D. Kazantzi, C. Kalogeropoulou and L. I. Costaridou, "Texture-based identification and characterization of interstitial pneumonia patterns in lung multidetector CT," IEEE transactions on information technology in biomedicine: a publication of the IEEE Engineering in Medicine and Biology Society 14, 675-680 (2010).
11. J. Yao, A. Dwyer, R. M. Summers and D. J. Mollura, "Computer-aided diagnosis of pulmonary infections using texture analysis and support vector machine classification," Academic radiology 18, 306-314 (2011).
12. R. W. Conners and C. A. Harlow, "A theoretical comparison of texture algorithms," IEEE transactions on pattern analysis and machine intelligence 2, 204-222 (1980).
13. R. W. Conners, M. M. Trivedi and C. A. Harlow, "Segmentation of a high-resolution urban scene using texture operators.," Comput Vision Graph 25, 273-310 (1984).
14. R. O. Duda, P. E. Hart and D. G. Stork, Pattern classification. (Wiley, 2001).
15. A. R. Webb and K. D. Copsey, Statistical Pattern Recognition. (Wiley, 2011
16. C. Liu and H. Wechsler, "Robust coding schemes for indexing and retrieval from large face databases," IEEE transactions on image processing: a publication of the IEEE Signal Processing Society 9, 132-137 (2000).
17. C. Cortes and V. Vapnik, "Support-vector networks," Mach Learn 20, 273-297 (1995).
18. Aerts, H. J., et al., Decoding tumour phenotype by noninvasive imaging using a quantitative radiomics approach. Nat Commun, 2014. 5: p. 4006.

The relevant portions of the references identified herein are incorporated herein by reference.

What is claimed is:

1. A method for analyzing three-dimensional image data of a target region of a subject, the method comprising:
   receiving, at a computer, the three-dimensional image data, the computer comprising a processor and a computer readable medium storing the three-dimensional image data and a computer program comprising coded instructions executable by the processor to perform the operations of:
   accessing, by the processor, the three-dimensional image data comprising a plurality of voxels;
   segmenting, by the processor, the three-dimensional image data using at least one window setting comprising a predetermined window width and a predetermined window level, to identify a region of interest within the target region containing imaging information predictive of a disease state of the target region;
   calculating, by the processor, at least two radiomic features associated with the region of interest;
   generating a decision line based on a training data set comprising a plurality of three-dimensional image data sets; and
   classifying, by the processor, the region of interest based on the calculated radiomic features, by comparing the at least two radiomic features to the decision line.

2. The method of claim 1 wherein the at least two radiomic features are calculated from gray-level co-occurrence matrices associated with the region of interest.

3. The method of claim 1 wherein the region of interest is classified using a classifier.

4. The method of claim 3 wherein the classifier is one of a linear Bayes normal classifier, a quadratic Bayes normal classifier and a support vector classifier.

5. The method of claim 1 wherein the step of identifying the region of interest comprises detecting a region having ground glass opacity.

6. The method of claim 1 wherein the target region is the subject's lung, liver, brain, prostate, kidney, head or neck.

7. The method of claim 1 wherein each radiomic feature is one of a first-order texture feature and a second-order texture feature.

8. The method of claim 7 wherein the first-order texture feature is one of mean absolute deviation and standard deviation.

9. The method of claim 7 wherein the second-order texture feature is at least one selected from the group consisting of: energy, entropy, correlation, inverse difference moment, inertia, cluster shade, and cluster prominence.

10. The method of claim 1 wherein the region of interest is classified as one of recurrent cancer and radiation induced lung injury.

11. The method of claim 1 further comprising:
presenting image data representing at least the region of interest on a display unit.

12. An apparatus for analyzing three-dimensional image data of a target region of a subject, the apparatus comprising:
memory storing three-dimensional image data of the target region of the subject; and at least one processor communicating with the memory and analyzing the three-dimensional image data, the processor configured to:
access, by the processor, the three-dimensional image data comprising a plurality of voxels;
segment the three-dimensional image data using at least one window setting comprising a predetermined window width and a predetermined window level, to identify a region of interest within the target region containing imaging information predictive of a disease state associated with the target region;
calculate at least two radiomic features associated with the target region;
generate a decision line based on a training data set comprising a plurality of three-dimensional image data sets; and
classify the region of interest based on the calculated radiomic features by comparing the at least two radiomic features to the decision line.

13. The apparatus of claim 12 wherein the processor is further configured to calculate the at least two radiomic features from gray-level co-occurrence matrices associated with the region of interest.

14. The apparatus of claim 12 wherein the region of interest is classified using a classifier.

15. The apparatus of claim 14 wherein the classifier is one of a linear Bayes normal classifier, a quadratic Bayes normal classifier and a support vector classifier.

16. The apparatus of claim 12 wherein the processor is further configured to identify the region of interest by detecting a region having ground glass opacity.

17. The apparatus of claim 12 wherein the target region is the subject's lung, liver, brain, prostate, kidney, head or neck.

18. The apparatus of claim 12 wherein each radiomic feature is one of a first-order texture feature and a second-order texture feature.

19. The apparatus of claim 18 wherein the first-order texture feature is one of mean absolute deviation and standard deviation.

20. The apparatus of claim 18 wherein the second-order texture feature is at least one selected from the group consisting of: energy, entropy, correlation, inverse difference moment, inertia, cluster shade, and cluster prominence.

21. The apparatus of claim 12 wherein the region of interest is classified as one of recurrent cancer and radiation induced lung injury.

22. The apparatus of claim 12 further comprising a display unit, wherein the processing structure is configured to present image data representing at least the region of interest on the display unit.

23. A non-transitory computer-readable medium having stored thereon program code for execution by a computer processor to perform a method for analyzing three-dimensional image data of a target region of a subject comprising:
accessing, by the computer processor, the three-dimensional image data comprising a plurality of voxels;
segmenting the three-dimensional image data using at least one window setting comprising a predetermined window width and a predetermined window level, to identify a region of interest within the target region containing imaging information predictive of a disease state of the target region;
calculating at least two radiomic features associated with the region of interest;
generating a decision line based on a training data set comprising a plurality of three-dimensional image data sets; and
classifying the region of interest based on the calculated radiomic features by comparing the at least two radiomic features to the decision line.

* * * * *